United States Patent [19]

Cole

[11] Patent Number: 4,779,625

[45] Date of Patent: Oct. 25, 1988

[54] DAMPING DEVICE FOR CIRCULATORY PRESSURE MEASURING APPARATUS

[75] Inventor: James E. Cole, Ventura, Calif.

[73] Assignee: Spectramed, Inc., Newport Beach, Calif.

[21] Appl. No.: 864,161

[22] Filed: May 16, 1986

[51] Int. Cl.$^4$ .............................................. A61B 5/02
[52] U.S. Cl. .................................. 128/673; 128/748; 73/707; 73/756
[58] Field of Search ............................. 128/672–673, 128/675, 748, 674; 73/707, 756; 137/269; 251/118

[56] References Cited

U.S. PATENT DOCUMENTS

| | | | |
|---|---|---|---|
| 3,665,948 | 5/1972 | Hohberger | 73/707 X |
| 3,865,100 | 2/1975 | Kanai et al. | 73/707 X |
| 4,335,729 | 6/1982 | Reynolds et al. | 128/748 X |
| 4,431,009 | 2/1984 | Marino, Jr. et al. | 128/673 |
| 4,509,946 | 4/1985 | McFarlane | 128/673 X |
| 4,517,844 | 5/1985 | Powell | 128/672 X |

FOREIGN PATENT DOCUMENTS 1588584 4/1981 United Kingdom ................. 73/707

Primary Examiner—Kyle L. Howell
Assistant Examiner—Angela D. Sykes
Attorney, Agent, or Firm—Lyon & Lyon

[57] ABSTRACT

A damping device for use in conjunction with a circulatory pressure measuring system to attenuate resonant pressure waves therein includes a series connector for connection to the pressure measuring system. An integrally connected parallel portion includes a capillary tube fluid resistance element in communication with the series connector. A flexible membrane isolates the capillary tube from a fixed volume gas chamber located adjacent the flexible membrane.

10 Claims, 2 Drawing Sheets

DAMPING DEVICE FOR CIRCULATORY PRESSURE MEASURING APPARATUS

BACKGROUND OF THE INVENTION

The instant invention relates to a damping device for use in combination with a fluid pressure measuring apparatus-transducer system used for measurement of circulatory pressure in a patient.

It is well known in the art to measure the circulatory pressure or blood pressure of a patient by inserting a catheter into an artery of the patient, the catheter having been prefilled with physiological saline solution. The incompressible saline solution transmits pressure waves generated by the heart and modified by other portions of the circulatory system, to a transducer which is coupled to the patient's circulatory system by the column of saline solution.

It has, however, been found in the past that inaccurate readings can be generated by the use of such a system. In particular, it has been found that compliant portions of the combined patient and measurement system which include the elastic walls of the patient's circulatory system, as well as the compliant or elastic walls of the pressure measuring apparatus cause the combination of the patient's circulatory system and the pressure measuring apparatus to have one or more resonant modes. As a result of the resonant modes, circulatory pressure waves having components at or near the resonant frequencies of the system tend to be distorted in that the amplitudes of the resonant frequency components rapidly increase within the system. This often causes the health care professional using the pressure measuring system as a diagnostic tool to misread the pressure within the system and hence to misdiagnose the condition of the patient. This problem is often referred to as "ringing" or "harmonic ringing".

A number of damping devices have been proposed or built to solve the ringing problem. U.S. Pat. No. 4,335,729 to Reynolds, et al. for APPARATUS AND METHOD FOR SUPPRESSING RESONANCE AND AN ELECTROMANOMETRY SYSTEM teaches one such damping device. Details of the damping device may best be seen in FIGS. 5 and 6 of Reynolds, et al. wherein a damper having a resistance pathway which is connected in parallel to a patient-transducer circuit is employed. The damper also has a gas filled cap in communication with the resistance pathway. It should be noted, however, in order to "tune out" the resonant frequencies of the monitoring system, it is necessary to rotate the enlarged head 132, thereby effectively changing the hydraulic or pneumatic resistance of the resistance passageway. Although this would seem to be an adequate solution, it has been found that, in practice, health care professionals do not have sufficient time to tune such a system to attenuate the resonant modes of a particular patient and pressure measuring apparatus configuration due to the necessity to repeatedly change the effective resistance of the resistance channel while observing the results on a monitor.

A similar adjustable system is disclosed in U.S. Pat. No. 4,431,009 to Marino, Jr., et al. for APPARATUS FOR MEASURING BLOOD PRESSURE. The damping device may best be seen in the sectional view of FIG. 2 wherein the damping device is connected in series between the patient and the pressure transducer. Adjustment of the valve needle 48 varies the hydraulic resistance of the patient-transducer circuit thereby changing the frequency to be attenuated by the damper. This system, however, suffers from the same faults as the Reynolds, et al. system due to the fact that it also must be adjusted manually after having been connected to a patient to remove resonant mode artifacts.

A different approach is taken in U.S. Pat. No. 4,517,844 to Powell, for FLUID DAMPING DEVICE FOR A COMPLIANT SYSTEM. In the Powell system a fixed resistance path 106 is connected in parallel to the primary patient-transducer path. A compliant gas cavity or parallel capacitance device 94 is threadedly connected to the resistance path. Powell also discloses a damping device whereby the patient-transducer system may be tuned by interchanging a plurality of compliant gas cavities of various sizes in order to effect tuning of the system. This damping device would also seem to suffer from the problems of the other prior art systems in that the active intervention of a health care professional would be needed to tune out the resonant modes of the system by interchanging removable parallel capacitances. In addition, it is clear that if the pressure measuring system had been connected to a patient for tuning, disconnection of the compliant gas cavity from the pressure measuring system followed by reconnection might result in significant risk of contaminating the saline solution with air bubbles, bacteria, pyrogens, viruses and the like and causing an infection in the patient.

Accordingly, what is needed is an improved damping device which effectively damps out resonant frequencies of pressure waves in a physiological pressure monitor, but which need not be adjusted by the health care professional in order to remove resonant frequencies after being connected to a particular patient.

SUMMARY OF THE INVENTION

A damping device for a physiological pressure measuring apparatus is disclosed herein. The damping device includes a tubular connector or conduit having an internal bore. The tubular connector terminates at a pair of luer-lock connectors at opposite ends thereof. A parallel circuit portion is formed integral therewith and includes a perpendicularly extending body having a capillary tube accepting bore formed therein. A capillary tube is seated within the bore in direct fluid communication with an internal bore of the conduit. A flexible sealing member encloses an end of the capillary tube opposite the end connected into the conduit. A cap is fitted over the membrane and defines a gas tight compliant volume.

One of the luer-lock connectors is connected to a patient circuit of a circulatory pressure measuring system. The other of the luer-lock connectors is connected to a transducer circuit of the circulatory pressure measuring system so that the damping device selectively absorbs resonant frequency components of pressure waves in order that the transducer can represent accurately, the pressure conditions within the circulatory system of the patient without artificially amplifying the resonant frequencies of the pressure measuring system.

A principal object of the present invention is to provide a damping device for a circulatory pressure measuring apparatus having a fixed fluid resistance and a fixed fluid capacitance which need not be adjusted to absorb resonant frequency pressure waves within the circulatory pressure measuring system.

Another object of the instant invention is to provide a damping device having a pressure conductive isolating member between the fixed fluid resistance and the fixed fluid capacitance in order to prevent introduction of gas bubbles, pyrogens, bacteria, viruses and other contaminants into the saline solution.

It is still another object of the instant invention to provide a damping device formed integrally of moldable, clear plastic which may be easily and inexpensively manufactured.

Other objects and uses of the present invention will become obvious to one skilled in the art upon a perusal of the following specification and claims in light of the accompanying drawings.

DESCRIPTION OF THE PREFERRED EMBODIMENT

Figure 1:
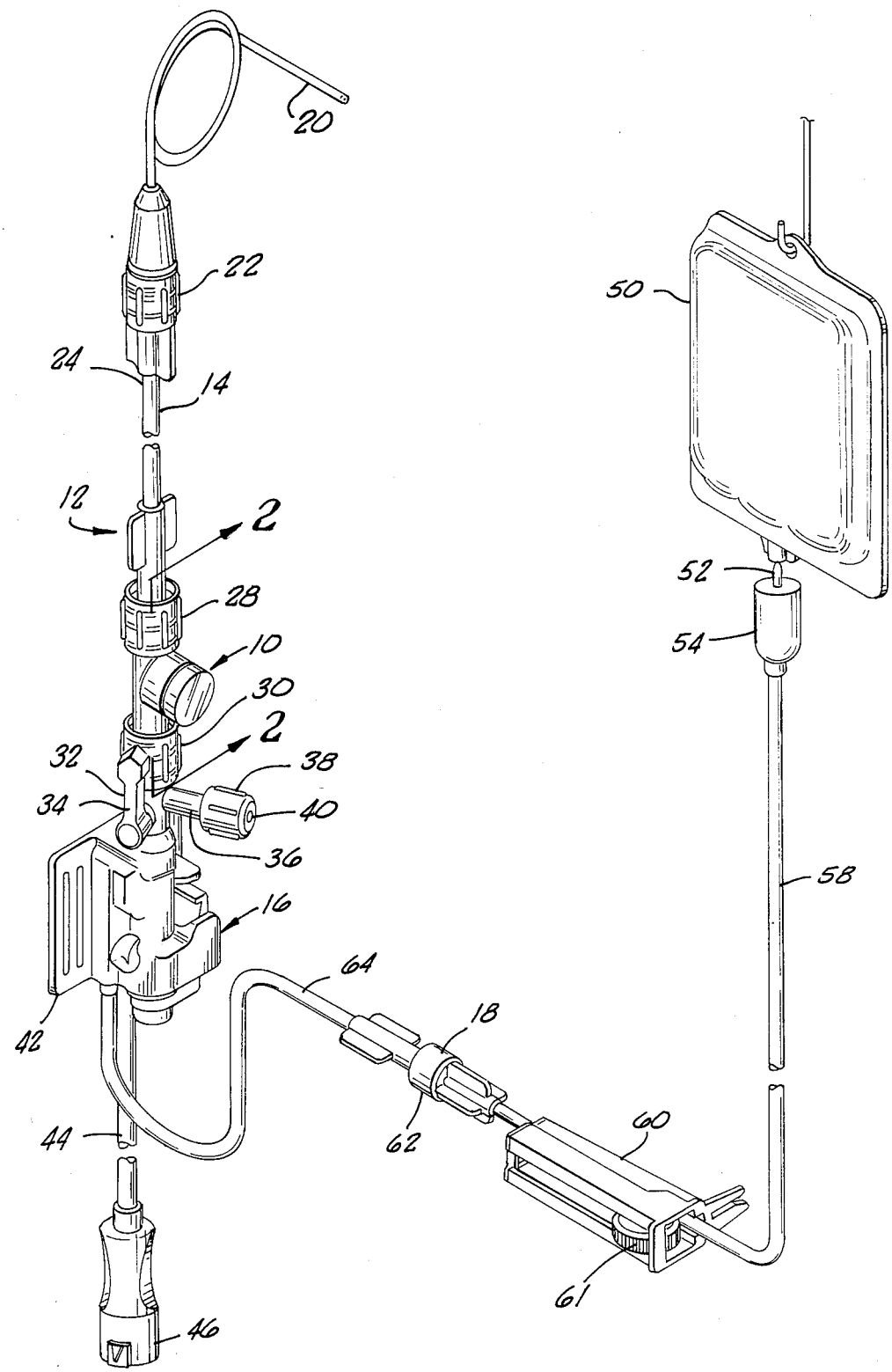
FIG. 1 is a perspective view of a circulatory pressure measuring system having included therein a damping device embodying the present invention.

Referring now to the drawings and especially to FIG. 1, an improved damping device, generally indicated by numeral 10 and embodying the present invention, is shown therein. The damping device 10 is connected in a circulatory pressure measuring system 12 comprising a patient circuit 14 connected to the damping device 10, a pressure measuring circuit 16 also connected to the damping device 10 and an intravenous supply circuit 18 connected to the pressure measuring circuit 16.

The patient circuit 14 includes a conventional circulatory pressure measuring catheter 20, which is adapted to be inserted into an artery of a patient to measure a circulatory pressure therein. The pressure measuring catheter 20 is filled with saline solution and is connected via a luer-lock connector 22 to a tube assembly 24 which also is filled with physiological saline solution. A female luer-lock connector 26 is connected with the tube assembly 24 and is threadedly interfitted with a male luer-lock connector 28 of the damping device 10. A luer-lock connector nut 30 connects the damping device 10 to a combination valve and vent 32. The valve and vent 32 has a stopcock type valve controlled by a lever 34. In the drawing of FIG. 1 the lever 34 is positioned in the transducer off position to allow fluid flow from the stopcock through a vent pipe 36 formed integral therewith and a vent cap 38 having a bore 40 formed therein in order to purge air from the system as it is being filled with saline solution.

A disposable pressure transducer 42 of the type which may be purchased from the Cardiovascular Products Division of Gould Inc. under model designation DTX is connected to the valve 32 and comprises a portion of the transducer circuit 16. An electrical lead assembly 44 is connected to the transducer assembly 42. A transducer plug assembly 46 is connected to the electrical lead 44 to conduct electrical signals from the transducer 42 indicative of monitored circulatory pressure to a suitable electronic processing device which is not shown, but is conventional in the art.

The intravenous supply circuit 18 includes a conventional intravenous bag 50 connected via a spike 52 to a drip chamber 54. The drip chamber 54 is connected to a tube 58 around which a conventional roller clamp assembly 60 is fitted. The roller clamp assembly 60 has a roller 61 to control fluid flow. The tube 58 is connected via a luer-lock connector 62 to a tube 64. The tube 64 is connected to the pressure transducer 42. In use, the intravenous bag 50 may be filled with a typical fluid component such as physiological saline solution which is allowed to flow through the drip chamber 54, fill the tube 58 and the fluid receiving portions of the disposable transducer 42. The physiological saline solution also fills a portion of the damping device 10, as will be seen hereinafter. The tube 14 and the catheter 20 are also filled with the saline solution to provide a liquid or incompressible fluid connection between the blood stream of the patient and the disposable transducer assembly 42 in order to provide excellent pressure transmission characteristics thereto. The rate at which the physiological saline is metered into the patient through the catheter 20 is controlled by a flow device built into the disposable transducer 42 as is well known in the art. It is necessary to allow the saline to be infused into the patient relatively slowly to maintain the end opening of the catheter 20 patent by preventing the formation of blood clots thereon.

Pressure impulses generated in the patient's circulatory system are transmitted by the saline solution in the catheter 20 through the tube 14, the damping device 10, and the valve assembly 32 to the disposable transducer 42 where the pressure waves are converted into electrical signals carried by the cable or electrical lead 44 to the transducer plug assembly 46 and supplied to a suitable monitoring device.

One of the problems encountered with the prior art monitoring systems which did not employ a damping device was that such systems exhibited resonant modes in their pressure wave transmitting characteristics which preferentially amplified the resonant frequencies present in the pressure waves from the patient. As a result of the resonant modes, certain monitored frequencies would be much higher in amplitude than normally found in the patient and hence could skew or distort the readings provided to the monitoring equipment. As was stated above, a number of variable control damping devices have been disclosed in the prior art. However, they have all been found difficult to use in practice due to the fact that they must be adjusted in a very time consuming manner by health care professionals.

Figure 2:
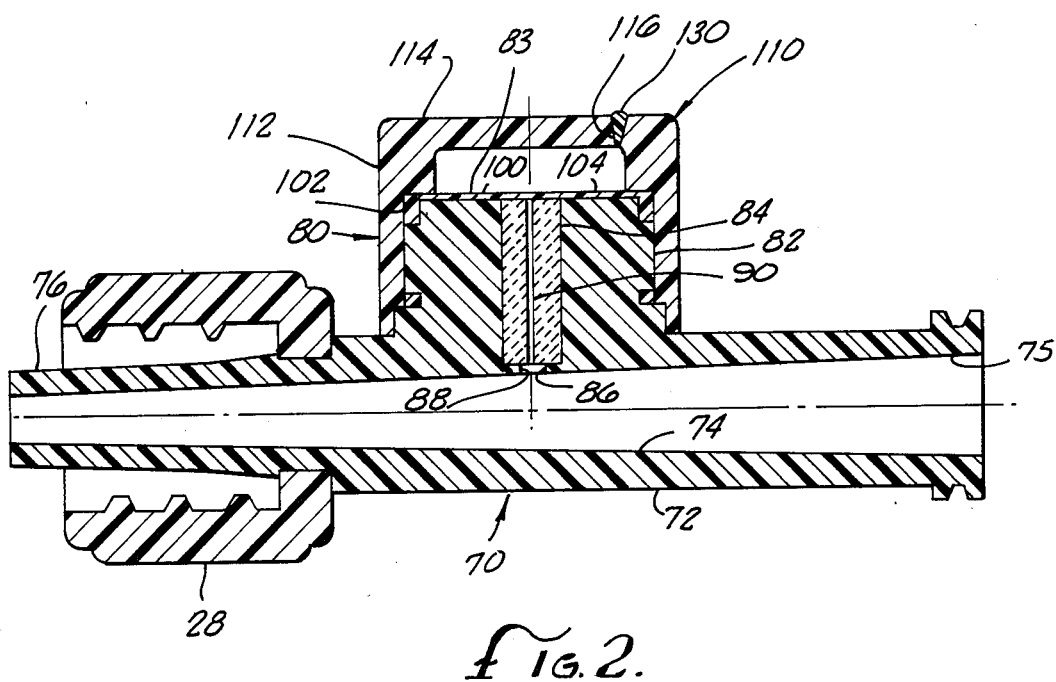
FIG. 2 is a sectional view taken substantially along line 2—2 of FIG. 1, showing details of the interior construction of the damping device embodying the present invention.

The inventive damping device 10 is considerably different than those disclosed in the prior art. The damping device 10, as may best be seen by referring to FIG. 2 includes a moldable plastic interconnecting tube 70 having an exterior wall 72 of substantially cylindrical shape. An interior circular cross-sectional bore 74 having a taper formed therein, defines a fluid conducting passage from the male luer-lock fitting 28 to the luer-lock connected 30. The bore 74 includes a luer-lock accepting taper 75 at one end. The conduit 70 tapers at the other end to a male member 76 which is interfitted into the luer-lock fitting 28.

The damping device 10 includes a parallel circuit portion 80 formed integral with the conduit portion 70. The parallel circuit portion 80 includes a pedestal body 82 having a top face portion 83 and a bore 84 formed therein. The bore 84 is positioned substantially at right angles to the bore 74 of the conduit 70. The bore 84 ends in a stepped portion 86 and a reduced diameter bore portion 88. A capillary tube 90 comprising a glass capillary tube having a 0.009 inch internal bore 92 formed therein and a length of 0.25 inches is interfitted within the bore 84. The capillary tube 90 comprises a resistance passage or a resistive pathway. It should be appreciated that the diameter of the bore 92 is much smaller than the internal diameter of 0.060 inches of the tube 14.

A flexible isolation membrane 100 comprised of silicone rubber and having a peripheral shoulder portion 102 and a sealing portion 104 is interfitted over the glass capillary tube 90 to seal the contents of the glass capillary tube 90 and the conduit 74 from any areas above the membrane 100. The flexible isolation membrane 100, in the preferred embodiment, has a thickness of 0.010 inches.

A cap 110 having a cylindrical sidewall 112 and a circular integral top portion 114 with a vent aperture 116 formed therein is interfitted over the membrane 100 and extends downward over the pedestal region 82 to seal the pedestal region and to define a compliant gas chamber 120 above the membrane 100. In the present embodiment the compliant gas chamber has a volume of 0.0054 cubic inches. The cap is ultrasonically welded to the pedestal 82 and traps the membrane 100 between a shoulder portion 122 of the cap and the top face portion 83 of the pedestal 82. Since the gas trapped within the chamber 120 might be under pressure above atmospheric pressure due to heating taking place in the ultrasonic welding operation, the vent 116 is provided to allow the gas to escape. Once the system has returned to atmospheric pressure, a seal 130 consisting of an ultraviolet light curable epoxy resin is inserted in the aperture 116 to seal the compliant gas chamber or compliant capacitance 120 from the outside environment.

As was stated above, the damping device 10 is connected in series with the patient circuit 12 and the pressure monitoring circuit 16. The conduit 70 is flooded with physiological saline solution to transmit the pressure waves between the patient and the disposable transducer 42. The relatively small diameter of the glass capillary tube bore 92 prevents significant entrainment of liquid within the capillary tube 90. The membrane 100 prevents intermixing of the contents of the gas compliant chamber 120 with the contents of the conduit 74 and also effectively increases the elastic constant of the compliant chamber 120. The combination of the very small bore capillary tube 90, the elastic membrane 100 and the compliant gas chamber 120 results in a damper which provides overdamping of a wide range of resonant frequencies of the monitoring system from 10 Hz. to 50 Hz. usually encountered in the typical physiological pressure monitoring situation.

As a result, the small bore capillary tube 90 gives relatively broad tuning for attenuating the commonly encountered resonant frequencies and eliminates the need to provide either an adjustable compliant volume or an adjustable resistance tube, as is taught and suggested in the prior art.

Thus, the damping device 10 need merely be incorporated in the typical circulatory pressure monitoring system in order to damp out the resonant pressure waves which would normally reach the transducer and create artifacts which might lead to misinterpretation of the data.

In the event that a circulatory pressure measuring system having resonant characteristics significantly different than the typical resonant characteristics of circulatory pressure measuring systems encountered in clinical use is to be employed the disclosed capillary tube having the 0.009 inch internal bore may have substituted therefor a capillary tube having an internal bore of 0.007 inches or the like. Thus, in the event that it does prove necessary to change the overall response characteristics of the damping device 10, a capillary tube of 0.007 inches bore may be substituted for the capillary tube 90 having the 0.009 inches capillary bore or the thickness of the membrane 100 may be increased.

It may be appreciated then that the instant invention provides a damping device which need not be adjusted by a health care professional and which provides overdamping for a typical circulatory pressure measuring system. The damping device 10 includes a very narrow resistance pathway which provides a wide range of damping frequencies for the system. The damping device 10 also includes an elastic internal membrane 100 which seals the resistance pathway from the compliant chamber 120 to provide both an increased compliance and isolation of the resistive pathway and hence the fluid conduit from the gas chamber 120 in order to protect the patient.

While there has been illustrated and described a particular embodiment of the present invention, it will be appreciated that numerous changes and modifications will occur to those skilled in the art and it is intended in the appended claims to cover all of those changes and modifications which fall within the true spirit and scope of the present invention.

What is claimed as new and desired to be secured by Letters Patent is:

1. A damping device for attenuating resonant frequency pressure waves in as circulatory pressure measuring system, comprising: a series connector; a fixed fluid resistance branch connector connected in parallel with said series connector; a substantially fixed volume gas cavity in proximity to said fixed fluid resistance connector; and means forming a flexible sealing member effective to extend the damping range of the device separating said fluid resistance branch connector from said gas cavity.

2. A damping device for attenuating resonant frequency pressure waves in a circulatory pressure measuring system, comprising: resistance means for providing a parallel fixed fluid resistance to a patient circuit of said blood pressure measuring system; capacitance means in communication with said resistance means for providing a fixed volume gas capacitance; and means forming a flexible partition adapted to extend the damping range of the device.

3. A damping device for use in conjunction with a circulatory pressure measuring apparatus to absorb selectively pressure waves having a frequency substantially equal to a resonant frequency of said circulatory pressure measuring apparatus, comprising: a series connector tube having a first end connector and a second end connector, said first end connector being connectable in series with a patient circuit portion of a circulatory pressure measuring apparatus in communication with a circulatory system of a patient, said second end connector being series connectable to a pressure measuring transducer so that a pressure wave transmitting path is defined between said patient and said pressure measuring transducer; a resonant energy bypass section formed integral with said series connector and having a bore defined therein; a capillary tube mounted within said bore; means forming a flexible elastic membrane enclosing the downstream end of said capillary tube and effective to extend the damping range of the device, a fluid reservoir connected in proximity with said flexible elastic membrane to receive pressure waves therefrom, said capillary tube having a diameter sized to act in conjunction with said membrane and said fluid reseervir so as to cause said damping device to be selectively excited by a resonant frequency of the circulatory pressure measuring apparatus and to attenuate the pressure waves of resonant frequency before they reach the pressure transducer.

4. A damping device for use in conjunction with a circulatory pressure measuring apparatus to absorb selectively pressure waves having a frequency substantially equal to a resonant frequency of said circulatory pressure measuring apparatus, as defined in claim 5, wherein said bore of said capillary tube is smaller than a bore of said patient circuit.

5. A damping device for use in conjunction with a circulatory pressure measuring apparatus to absorb selectively pressure waves having a frequency substantially equal to a resonant frequency of said circulatory pressure measuring apparatus, as defined in claim 5, wherein said series connector is formed integral with said first end connector and said second end connector.

6. The damping device as recited in any one of claims 3, 4, or 5 in which said fluid reservoir is a gas reservoir.

7. A damping device for attenuating resonant frequency pressure waves in a circulatory pressure measuring system, comprising: fixed resistance passage means connected in parallel to a patient circuit of a circulatory pressure measuring system; a chamber containing a compliant, substantially fixed volume of gas in proximity to the downstream end of said fluid resistance passage means; and means forming a flexible, pressure conducting partition effective to extend the damping range of the device separating said fluid resistance passage means from said chamber.

8. A damping device for attenuating resonant frequency pressure waves in a circulatory pressure measuring system comprising: fluid resistance passage means comprising a capillary tube connected in parallel to a patient circuit of a circulatory pressure measuring system; fixed fluid capacitance means comprising a chamber containing a compliant, substantially fixed volume of gas in proximity to the downstream end of said fluid resistance means; and means forming a flexible, pressure conducting membrane effective to extend the damping range of the device separating said fluid resistance means from said fluid capacitance means.

9. The damping device as recited in any one of claims 1, 2 to 5, 7 or 8 effective to damp resonant frequencies in the range of from 10 Hz to 50 Hz.

10. The damping device as recited in claim 9, effective to damp resonant frequencies in the range of about 40 Hz.

* * * * *